United States Patent [19]

Elden

[11] Patent Number: 5,890,489
[45] Date of Patent: Apr. 6, 1999

[54] METHOD FOR NON-INVASIVE DETERMINATION OF GLUCOSE IN BODY FLUIDS

[75] Inventor: Harry Richardson Elden, Miami, Fla.

[73] Assignee: Dermal Therapy (Barbados) Inc., Bridgetown, Barbados

[21] Appl. No.: 688,650

[22] Filed: Jul. 30, 1996

(Under 37 CFR 1.47)

Related U.S. Application Data

[63] Continuation-in-part of Ser. No. 636,454, Apr. 23, 1996, abandoned.

[51] Int. Cl.$^6$ ..................................................... A61B 19/00
[52] U.S. Cl. ............................................. 128/898; 600/547
[58] Field of Search ............................... 128/898; 435/14; 600/306, 307, 309, 310, 316, 326, 346, 347, 365, 547

[56] References Cited

U.S. PATENT DOCUMENTS

| | | | |
|---|---|---|---|
| 2,812,757 | 11/1957 | Lusk et al. | 600/547 |
| 4,178,916 | 12/1979 | McNamara | 600/547 |
| 4,365,637 | 12/1982 | Johnson | 600/547 |
| 4,746,508 | 5/1988 | Carey et al. | |
| 4,966,158 | 10/1990 | Homma et al. | 600/547 |
| 5,036,861 | 8/1991 | Sembrowich et al. | |
| 5,115,133 | 5/1992 | Knudson . | |
| 5,139,023 | 8/1992 | Stanley et al. | |
| 5,140,985 | 8/1992 | Schroeder et al. | |
| 5,146,091 | 9/1992 | Knudson . | |
| 5,179,951 | 1/1993 | Knudson . | |
| 5,222,496 | 6/1993 | Clarke et al. | |
| 5,433,197 | 7/1995 | Stark . | |

FOREIGN PATENT DOCUMENTS

| | | | |
|---|---|---|---|
| 1934139 | 1/1971 | Germany . | |
| 363031638 | 2/1988 | Japan | 600/347 |
| WO 9318402 | 9/1993 | WIPO . | |
| WO 9502357 | 1/1995 | WIPO . | |
| WO 9504496 | 2/1995 | WIPO . | |

OTHER PUBLICATIONS

P. Lonnroth et al., "A Microdialysis Method Allowing Characterization of Intercellular Water Space in Humans", *Am. Physiol. Soc.* 253 (*Endocrinol. Metab. 16*):E228 (1987).

K.M. Halprin et al., "Glucose Entry into the Human Epidermis: II. The Penetration of Glucose into the Human Epidermis In Virto", *J. Invest. Derm.* 49(6):561 (1967).

H.R. Elden, "The Diffusion of Sodium Chloride, Hydrochloric Acid, and Copper Sulfate Through Glycerol–Water Mixtures" Doctoral Dissertation, The Catholic University of America Press, Washington, D.C., pp. 19–22 (1956).

Zamzow et al.: "Development and evaluation of a wearable blood glucose monitor", *ASAIO Transactions* 36(3):588–591, Toronto, Canada, 1990.

*Primary Examiner*—Mickey Yu
*Assistant Examiner*—Kelly O'Hara
*Attorney, Agent, or Firm*—Pennie & Edmonds LLP

[57] ABSTRACT

Method for non-invasively determining glucose level in fluid of subject, typically blood glucose level. A particular device is mounted on the skin of the patient for a fixed period of time. The device is mounted on the skin such that a substrate such as paper or gel or an aqueous glucose solution carried by the device are in contact with the patient's skin. Water and/or glucose migrates between the substrate or the aqueous glucose solution of the device. The degree of migration of the substance in question is monitored, for example the amount of glucose remaining in an aqueous solution of the device is measured at the end of the fixed period. This can be done by a conventional or other spectrophotometric method, for example. The glucose level is determined based on the degree of migration of the migrating substance. That is, the degree of migration is correlated with previously determined fluid glucose levels based on directly measured fluid glucose levels. In another approach, impedance alone is measured at the skin surface over a relatively short time period, even less than one second and the impedance is correlated with previously determined glucose levels. It is thus possible, through such a correlation, to routinely non-invasively determine fluid glucose levels.

8 Claims, 9 Drawing Sheets

METHOD FOR NON-INVASIVE DETERMINATION OF GLUCOSE IN BODY FLUIDS

This application is a continuation-in-part of U.S. patent application Ser. No. 08/636,454, filed Apr. 23, 1996 now abandoned.

FIELD OF THE INVENTION

The present invention relates to non-invasive methods and devices for determining the level of glucose in a body fluid of a subject.

BACKGROUND OF THE INVENTION

There are numerous reasons for determining the level of glucose present in body fluid of a subject. In the case of a person suffering from diabetes, it is often necessary to determine the glucose level in blood daily, or even more frequently. Non-invasive approaches to determination of blood glucose levels have been suggested in the patent literature. For example, U.S. Pat. No. 5,036,861 (issued to Sembrowich et al. on Aug. 6, 1991) describes a wrist-mountable device having an electrode which measures glucose present in sweat at the skin surface. U.S. Pat. No. 5,222,496 (issued to Clarke et al. on Jun. 29, 1993) describes an infrared glucose sensor mountable, for instance, on a wrist or finger. U.S. Pat. No. 5,433,197 (issued to Stark on Jul. 18, 1995) describes determination of blood glucose through illuminating a patient's eye with near-infrared radiation. U.S. Pat. Nos. 5,115,133, 5,146,091 and 5,197,951 (issued to Knudson on May 19, 1992, Sep. 8, 1992 and Jan. 19, 1993, respectively) describe measuring blood glucose within blood vessels of a tympanic membrane in a human ear through light absorption measurements. The specifications of all of these patents are incorporated herein by reference.

The most common current approaches to determining blood glucose levels still appear to involve obtaining a sample of the person's blood and then measuring the level of glucose in the sample. These approaches will not be reviewed here except to say that obtaining the blood sample necessarily involves an invasive technique. Generally, the person's skin is broken or lanced to cause an external flow of blood which is collected in some fashion for the glucose level determination. This can be both inconvenient and distressful for a person and it is an object of the present invention to avoid the step of obtaining a blood sample directly, at least on a routine or daily basis.

It is known that skin tissue, when immersed in an aqueous glucose solution, equilibrates linearly with the concentration of external glucose ("Glucose Entry into the Human Epidermis. I. The Concentration of Glucose in the Human Epidermis", K. M. Halprin, A. Ohkawara and K. Adachi, *J. Invest. Dermatol.*, 49(6): 559, 1967; "Glucose Entry into the Human Epidermis. II. The Penetration of Glucose into the Human Epidermis in vitro", K. M. Halprin and A. Ohkawara, *J Invest Derm.*, 49(6): 561, 1967). It has also been shown that that skin glucose can vary in synchrony with blood level glucose during standardized tolerance testing in vivo ("The Cutaneous Glucose Tolerance Test I. A, Rate Constant Formula for Glucose Disappearance from the Skin", R. M. Fusaro, J. A. Johnson and J. V. Pilsum, *J. Invest. Dermatol.*, 42: 359, 1964; "The Cutaneous Glucose Tolerance Test", R. M. Fusaro and J. A. Johnson, *J. Invest. Dermatol.*, 44: 230, 1965). It is also known that glucose levels equilibrate between blood and interstitial fluids in contact with blood vessels ("A Microdialysis Method Allowing Characterization of Intercellular Water Space in Human", P. Lonnroth, P.-A. Jansson and U. Smith, The *American Journal of Physiology*, 253 (Endocrinol. Metab., 16): E228–E231, 1987; "Assessment of Subcutaneous Glucose Concentration; Validation of the Wick Technique as a Reference for Implanted Electrochemical Sensors in Normal and Diabetic Dogs," U. Fischer, R. Ertle, P. Abel, K. Rebrin, E. Brunstein, H. Hahn von Dorsche and E. J. Freyse, *Diabetologia*, 30: 940, 1987). Implantation of dialysis needles equipped with glucose sensors has shown that orally ingested glucose load is reflected by parallel changes in skin tissue glucose.

SUMMARY OF THE INVENTION

The present invention is a method and apparatus for non-invasively monitoring levels of glucose in a body fluid of a subject. Typically, blood glucose levels are determined in a human subject.

In one embodiment, the invention is a method for monitoring the level of glucose in a body fluid by contacting a skin surface of the subject with a substrate capable of absorbing water to permit migration of water between the substrate and the skin. This is followed by monitoring the migration of water between the substrate and the skin and determining the amount of glucose in the body fluid based upon the monitored amount of water migration.

The body fluid can be interstitial body fluid, but blood glucose level is likely to be of more interest. In situations where the level of the constituent glucose is monitored to indirectly determine its level in another fluid, say by monitoring the level of glucose in interstitial fluid to determine the level of glucose in blood plasma, the interstitial body fluid must be reflective of the level in the other fluid.

The skin can be contacted with the substrate for a predetermined time period and monitoring the migration of water can be weighing the substrate subsequent to the contacting step. The time period can be anywhere between about 1 minute and about 2 hours, but a time period between about 5 minutes and about 1 hour is more preferred, but the time period can also be between about 10 minutes and about 45 minutes, between about 20 minutes and about 40 minutes or about 30 minutes.

The substrate can be paper. The substrate can have a contact area with the skin of between about 1 $cm^2$ and about 9 $cm^2$, or between about 2 $cm^2$ and about 6 $cm^2$. In the working embodiment described further below, the contact area was about 4 $cm^2$.

In embodiments described in detail below, the substrate bears a sufficiently small amount of water prior to the contacting step such that the migration of water is from the skin to the substrate during the contacting step.

The monitoring step can include measuring electrical resistance of the substrate in contact with the skin surface. The monitoring step can include determining the length of time it takes the measured resistance to change a fixed amount and correlating this change with blood glucose levels determined directly.

In a particular embodiment, the invention is a method for monitoring the level of glucose present in a body fluid of a subject which includes contacting a skin surface of the subject with an aqueous glucose solution of predetermined concentration to permit migration of the water and the glucose between interstitial skin fluid and the solution. The method includes monitoring the amount of glucose present in the solution and determining the amount of glucose in the body fluid based upon the monitored amount of glucose in the solution. The determination is generally based on a prior calibration in which amounts of migration have been correlated with directly measured body fluid amounts of glucose in question.

The blood glucose level of the subject can be determined based on the monitored amount of glucose in the solution.

In an embodiment described in detail below, the predetermined concentration of glucose in the solution is sufficiently high that migration of the glucose is from the solution and into the skin. The monitoring step can include determining the amount of the glucose in the solution after the substrate has been in contact with the skin for a predetermined length of time. The predetermined length of time can be between about 1 minute and about 2 hours; between about 5 minutes and about 1 hour; between about 10 minutes and about 45 minutes; between about 20 minutes and about 40 minutes; or about 30 minutes.

The aqueous solution can include a wetting agent, for example, propylene) glycol.

The concentration of glucose in the solution, prior to the contacting step would generally be between about 50 and about 1000 mgs/dL;

between about 200 and about 700 mgs/dL; between about 400 and about 600 mgs/dL; or about 475 mgs/dL.

In one arrangement, a semi-permeable membrane is located between the solution and the skin to provide indirect contact of the skin and solution therethrough during the contacting step.

As mentioned, the body fluid can be blood and non-invasively determining the amount of glucose in the blood can include correlating the determined concentration of glucose in the solution with directly determined blood glucose levels using previously determined data.

The volume of the solution can be between about 0.1 ml and about 1 ml; between about 0.2 ml and about 0.7 ml; between about 0.3 ml and about 0.5 ml; or about 0.4 ml.

The contact area between the skin and solution can be between about 0.05 in$^2$ (0.3 cm$^2$) and about 4 in$^2$ (25 cm$^2$); between about 0.2 in$^2$ (1.3 cm$^2$) and about 1 in$^2$ (6.5 cm$^2$); or about 0.4 in$^2$ (2.6 cm$^2$). The contact can be direct, or indirect, as through a semi-permeable membrane that permits diffusion of water and glucose.

The method can be performed using a hand-held device in which the solution is contained, the device including a solution contact area dimensioned for contacting the solution with a wrist of a human subject.

According to another embodiment of the invention, there is a method for monitoring glucose in a body fluid of a subject which includes contacting a skin surface of the subject with a substrate substantially free of glucose so as to permit migration of glucose between the body fluid and the substrate. The method also includes monitoring the amount of glucose present in the substrate and determining the amount of glucose in the body fluid based upon the monitored amount of the glucose in the substrate. According to this embodiment, the substrate is free of a glucose transport inhibitor or an exogenous source of energy, or the skin has not been induced to sweat. The substrate can be paper.

The body fluid can be interstitial body fluid, but again, blood glucose level is likely to be of more interest.

The skin can be contacted with the substrate for a predetermined time period and monitoring the amount of glucose present in the substrate can include determining the amount of glucose in substrate at the end of the time period.

In a method in which the substrate is paper, the amount of the glucose borne by the paper can be determined by transferring the paper to a pre-determined amount of water and determining the amount of glucose borne by the substrate based on the concentration of glucose dissolved in the water.

The concentration of glucose dissolved in the water can be determined spectrophotometrically. The determination can include reacting the glucose with a reagent to generate a chromophore which absorbs light in the visible range of the electromagnetic spectrum. The predetermined time period can be anywhere between about 1 minute and about 2 hours, but a time period between about 5 minutes and about 1 hour is more preferred, but the time period can also be between about 10 minutes and about 45 minutes, between about 20 minutes and about 40 minutes or about 30 minutes.

A paper substrate can have a contact area with the skin of between about 1 cm$^2$ and about 9 cm$^2$, between about 2 cm$^2$ and about 6 cm$^2$. In the working embodiment described further below, the contact area was about 4 cm$^2$.

According to another embodiment, the invention is a method for monitoring the blood glucose level of a subject which includes contacting a skin surface ol the subject with a substrate bearing a known amount of glucose, so as to permit migration of glucose between the skin and the substrate; monitoring the amount of the glucose in the substrate; and determining the blood glucose level of the subject based upon the monitored amount of glucose in the substrate.

The substrate can be paper or it can be a gel, particularly a water-based gel.

In a particular aspect, described further below, the known amount of glucose is sufficiently high that migration of the glucose is from the substrate and into the skin.

The skin can be contacted with the substrate for a predetermined time period and monitoring the amount of glucose present in the substrate can include determining the amount of glucose in the substrate after the time period. The amount of glucose borne by a 2 cm×2 cm paper, for example, prior to contact can be between about 0.05 and about 0.5 mgs, under particular circumstances, the preferred amount might be between about 0.1 and about 0.4 mgs, or even between about 0.2 and 0.3 mgs. The paper can be, for example, transferred after the contacting step to a pre-determined amount of water and the amount of glucose borne by the paper determined based on the concentration of glucose dissolved in the water. The concentration of glucose dissolved in the water can be determined spectrophotometrically. Further, spectrophotometric determination can include reacting the glucose with a reagent to generate a chromophore which absorbs light in the visible range of the electromagnetic spectrum.

The predetermined time period can be anywhere between about 1 minute and about 2 hours, but a time period between about 5 minutes and about 1 hour is more preferred, but the time period can also be between about 10 minutes and about 45 minutes, between about 20 minutes and about 40 minutes, or about 30 minutes.

A paper substrate can have a contact area with the skin of between about 1 cm$^2$ and about 9 cm$^2$, between about 2 cm$^2$ and about 6 cm$^2$. In the working embodiment described further below, the contact area was about 4 cm$^2$.

A gel substrate, as described below in connection with a particular embodiment, can have a semi-permeable membrane located between the substrate and the skin to provide indirect contact of the skin and gel therethrough during the contacting step.

The concentration of glucose in a gel substrate can be up to about 600 mgs/dL; or between about 50 and 500 mgs/dL, but depending upon circumstances the preferred amount might be between about 100 and 500 mgs/dL, or even somewhere between 200 and about 500 mgs/dL prior to the contacting step. Optimization would be carried out to determine the best concentration under particular circumstances, bearing in mind that a particular application, as already mentioned, requires that the glucose concentration be sufficiently high to permit migration of glucose from gel to the skin.

Another embodiment of the invention is a device for monitoring the level of blood glucose of a subject. The device includes a substrate bearing a known amount of glucose, the substrate having the property that the glucose can freely diffuse, when in contact with human skin, along a concentration gradient of the glucose between the substrate and skin, the substrate including a surface for said contact, and an occlusive covering.

The device can be hand-held device and have a contact area dimensioned for contact with a wrist of a human subject. The contact surface can be provided by a membrane permeable to glucose. The contact area can be between about 0.05 in$^2$ (0.3 cm$^2$) and about 4 in$^2$ (25 cm$^2$).

The substrate of device can be paper or a gel, particularly a water based gel. The volume of the gel can be between about 0.1 ml and about 1 ml. A device having a membrane can be provided with a releasable protective covering for the membrane.

The concentration of glucose in gel can be between about 50 mgs/dL and about 1000 mgs/dL.

Another device of the invention includes a well containing an aqueous glucose solution of predetermined concentration and a surface bearing a pressure-sensitive adhesive surrounding an upper portion of the well, to permit mounting of the device on a skin surface of the subject with the solution in contact with the skin surface.

The device can include means for obtaining a sample of the glucose solution from the well when the device is mounted on the skin surface. A preferred means is a membrane located to be accessible when the device is mounted on the skin surface and such that it may be punctured in order to obtain the sample.

Another embodiment of the invention is a method for non-invasively invasively monitoring glucose in a body fluid of a subject, which method includes measuring the degree of skin hydration of the subject and determining the amount of glucose in the body fluid based upon the degree of skin hydration.

In a particular embodiment, the body fluid is blood, and measuring the degree of skin hydration includes measuring Impedance at a site of the outer skin of the subject. The skin site might be on a forearm or a finger of a human subject, for example.

The degree of hydration can be measured for a period of time between about just more than 0 seconds and about 30 seconds; between about 0.5 seconds and about 10 seconds; between about 1 second and about 5 seconds; or the time period can be about 5 seconds.

According to a particular embodiment, a number of impedance measurements are taken over a short period of time, say a few seconds, or a few minutes, and the blood glucose determination is based on an average of the measurements.

BRIEF DESCRIPTION OF THE DRAWINGS

Preferred embodiments of the invention will now be described, reference being had to the accompanying drawings, wherein.

DETAILED DESCRIPTION OF PREFERRED EMBODIMENTS

Figure 1:
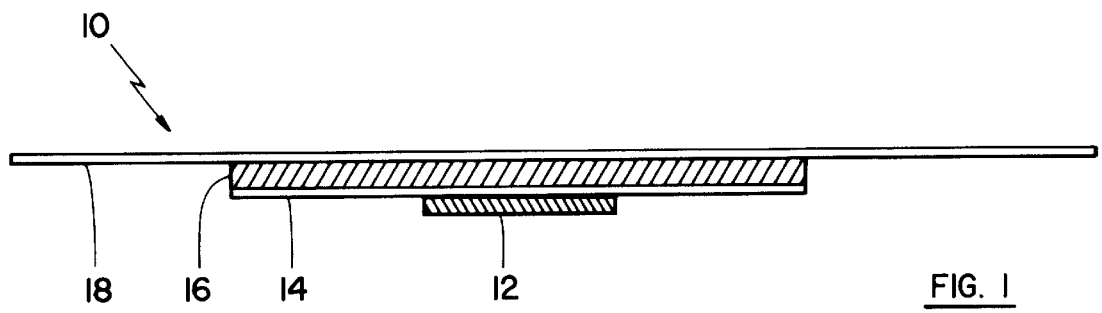
FIG. 1 shows a first embodiment device of the present invention in which the substrate is paper.

Turning to FIG. 1 of the drawings, patch device 10 includes absorbent paper strip 12, occlusive barrier 14, soft contour cushion 16, and adhesive top plastic bandage 18. Paper strip 12, can be, for example, a 2 cm×4 cm piece of chromatography paper (Whatman No. 1 Chr) folded over on itself to form a square. Occlusive barrier 14 is of an impermeable flexible plastic material bonded to soft contour cushion 16. Contour cushion 16 is bonded to plastic bandage material 18. Device 10 is placed over a skin site, typically the wrist, and held in place by ends of bandage 18 bearing a skin adhesive. The absorbent paper strip is then inserted between the skin and occlusive barrier 14 to permit transport of biochemicals of interest between the skin and the paper substrate. Such biochemicals of interest include glucose and water involved in monitoring the diabetic condition of skin.

Figure 1A:
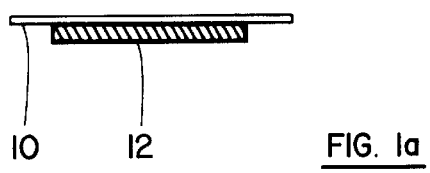
FIG. 1a shows a variant of the first embodiment device.

Alternatively, the absorbent paper strip may be positioned beneath a metal electrode 20 which is inserted between device 10 and the skin, as illustrated in FIG. 1a.

Figure 2:
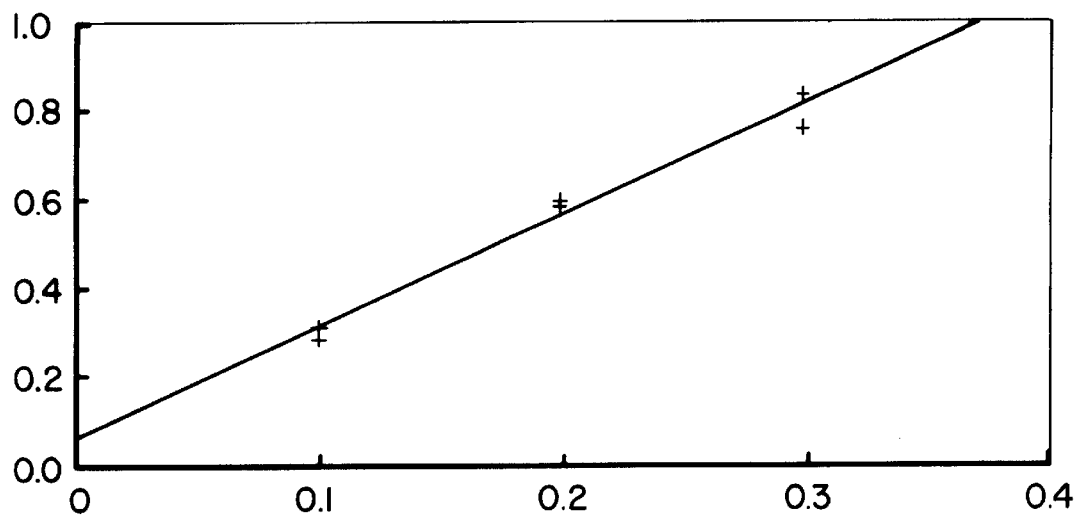
FIG. 2 is plot of spectral absorbance at 635 nm of the eluate of paper strips treated with glucose plotted against the amount (mgs) of glucose added to the strips. The eluate of the paper was treated with a Toluidine Glucose Reagent Kit, (#635, Sigma, St. Louis, Mo.)

In use, device 10 is placed over the skin site and fixed by attaching adhesive ends of bandage 18 to the skin. The absorbent paper substrate is inserted between the skin and occluded surface 14 of the device. In experiments described further below, a stock aqueous solution of glucose was made to the concentration required to provide a desired amount of glucose to be deposited by micropipette to the paper strip which was allowed to dry at room temperature prior to use. The amount of glucose remaining with the absorbent paper substrate after skin contact was determined by inserting the paper strip into a screw cap test tube. Test reagent (Toluidine Kit, #635-6, Sigma, St. Louis) was admitted, the cap attached and the mixture heated at 100° C. for 10 minutes. The color which developed was measured at a wavelength of 635 nm in 1 cm transmission spectral cells and the concentration of glucose present determined from the amount of spectral absorption. Absorbance as a function of known amounts of glucose added to paper strips is plotted in FIG. 2, to establish that observed absorbance is in proportion to the amount of glucose present.

Figure 3:
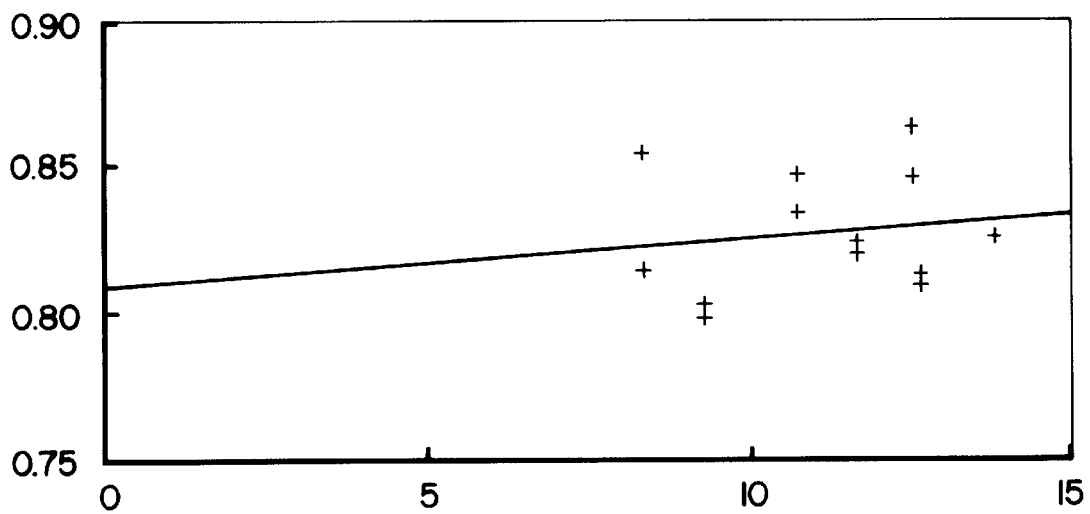
FIGS. 3 and 4 are representative plots of spectral absorbance (635 mm) of eluate of paper strips vs the directly determined blood glucose level of human subjects (mmol/L). For each point, the subject was treated for thirty minutes with a paper strip to which 0.1 ml of solution (glucose, 300 milligrams percent, and cholate sodium salt, 2 grams percent) had been applied and dried under ambient conditions. The eluate of each paper strip was treated with a Toluidine Glucose Reagent Kit and absorbance determined (y-axis). After the thirty minute exposure, a blood sample was taken from the subject and the blood glucose level determined directly from the sample using an Elite Glucometer (x-axis)
Figure 4:
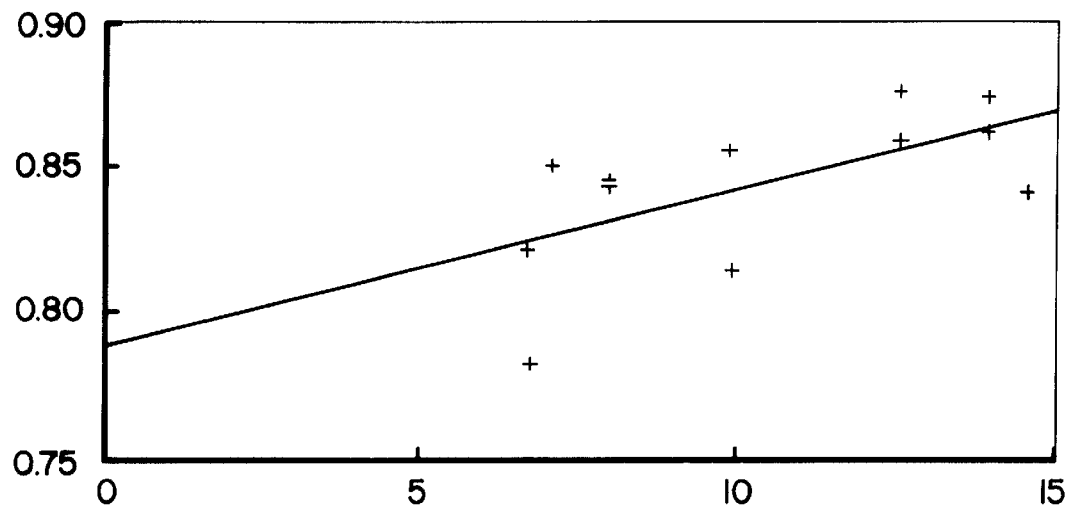

In one set of experiments, the chromatographic paper was loaded with 0.1 ml of a solution (glucose, 300 mgs percent and cholate sodium salt, 2 gms percent) and dried in room air. Cholates have been found to enhance penetration of glucose into an external hydrogel as described in U.S. Pat. No. 5,139,023 (issued to Carey et al.t on May 24, 1988), the specification of which is incorporated herein by reference. The amount of glucose remaining with the substrate after 30 minutes was plotted as a function of blood glucose determined directly from a blood sample using a lancet prick and measuring the blood glucose concentration using an Elite Glucometer (Miles Canada, Diagnostics Division, Division of Bayer). Typical results are shown in FIGS. 3 and 4. U.S. Pat. No. 4,746,508, the specification of which is incorporated herein by reference, describes bile salt analogs that have penetration enhancement properties.

Another set of similar experiments was carried out in which the chromatography paper was loaded with 0.10 ml of a solution (glucose, 300 mgs percent and urea, 10 gms percent) and dried in room air. The results are plotted in FIG. 5.

Figure 6:
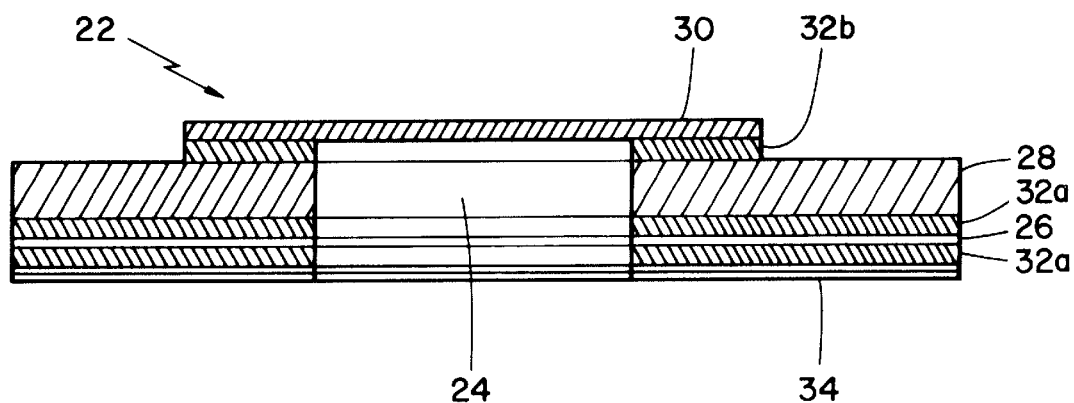
FIG. 6 shows a second embodiment device of the present invention.

Another embodiment of a device of the invention is patch device 22 shown in FIG. 6. Device 22 includes a substrate well 24 (Methocel gel 0.5%, Isotonic (sodium chloride) Gel, and buffered Isotonic Gel and gel with penetration enhancers such as urea, substituted ureas, cholates, lecithins, aliphatic alcohols, aliphatic acids, substituted aliphatic acids and emulsifiers), lower membrane material 26 (BioFill—biological skin substitute, microcrystalline cellulose, Productos Biotecnologicos S.A., Bom Retiro, Curitiba, Parana, Brazil), insert rubber ring 28 and upper impermeable transparent plate 30. The transparent plate could be replaced by a second membrane. Intermediate collar 32a, having adhesive on both its upper and lower surfaces, secures the lower membrane to the rubber ring. Upper collar 32b, having adhesive on both its upper and lower surfaces, secures transparent plate 30 to the rubber ring. Lowermost collar 32c, having adhesive on both its upper and lower surfaces, secures protective impermeable tape 34 to the underside of the device so that the tape covers lower membrane 26.

For use, the well is filled with a glucose solution and the device is closed by the upper impermeable plate and the bottom membrane. A skin site is prepared by wiping with a preparatory pad and allowed to dry. The lower protective paper is removed from the lower adhesive collar and the device is placed in contact with the skin. The inner diameter of ring would typically be between about 0.25 inches (0.64 cm) and about 0.5 inches (1.3 cm) and it could typically have a depth of between about 0.04 inches (0.1 cm) and about 0.16 inches (0.4 cm). These dimensions of course can be optimized in terms of the overall gel volume needed or desired and the surface area provided for exposure to person's skin in use. The lower collar typically has an outer diameter of about 1¼ inches (3.2 cm) and again the collar dimensions and adhesive used can be varied to obtain suitable adhesion of the device to a person's skin for the length of time it is to be adhered thereto.

Other possible materials that might be used as a membrane include membranous tissue material used to make Kling Tite™, Naturalamb™ natural skin condoms, Trojan™ premium product, Carter Wallace, Cranbury, N.J., USA, Cyclopore membranes, hydrophylic and hydrophobic, (Whatman Inc.), and Gelman membranes. Any semipermeable membrane that permits the solute(s) of interest to diffuse therethrough reproducibly would be suitable. Carbopol is a polymer of acrylic acid crosslinked with a polyfunctional agent (B.F. Goodrich). Another possible gel would be Methocel (Dow Chemical, Midland, Mich.), which is a water miscible polymer of hydroxypropyl methylcellulose. Other gelling agents include collagen, gelatin, silica gel and other hydrophilic materials which provide gel strength, dissolve the solute(s) of interest and permit diffusion of the solute(s). Gel solutions used may contain sufficient sodium chloride and sodium bicarbonate to establish isotonic conditions compatible with that of interstitial fluid. Isotonic gel, pH and other agents may be adjusted to facilitate penetration of glucose through stratum corneum. The membrane and gel must be compatible with each other in the sense that the membrane must retain the gel while permitting diffusion of the solute(s) of interest.

As with the paper substrate described above, the gel is usually loaded with glucose and the glucose concentration is chosen to be great enough to diffuse through the lower membrane and into the skin. It might be found preferable to manufacture more than one standard or pre-selected gel, say three gels, having low, medium and high glucose concentrations that each provide satisfactory performance under particular circumstances. For example, it might be found that a gel having a relatively high glucose concentration works particularly well for use following a heavy meal. The optimum value would be determined by the need to exceed the peak load while at the same time avoiding saturating the skin site, but at the same time the necessity of having a measurable difference between the initial and final levels of glucose in the substrate gel. It might be necessary to select based upon individual glucose tolerance curves. Optimization of sampling time might vary depending upon site glucose levels and the rate of transfer possible to achieve between the gel and site.

After a given length of time, device 22 is removed from the subject's skin. The glucose concentration in the gel is determined by inserting the electrometric probe of an Elite Glucometer into the gel and drawing a small amount of the solution, about 3 $\mu$l, into the probe. The glucometer yields a reading in about a minute.

Figure 7:
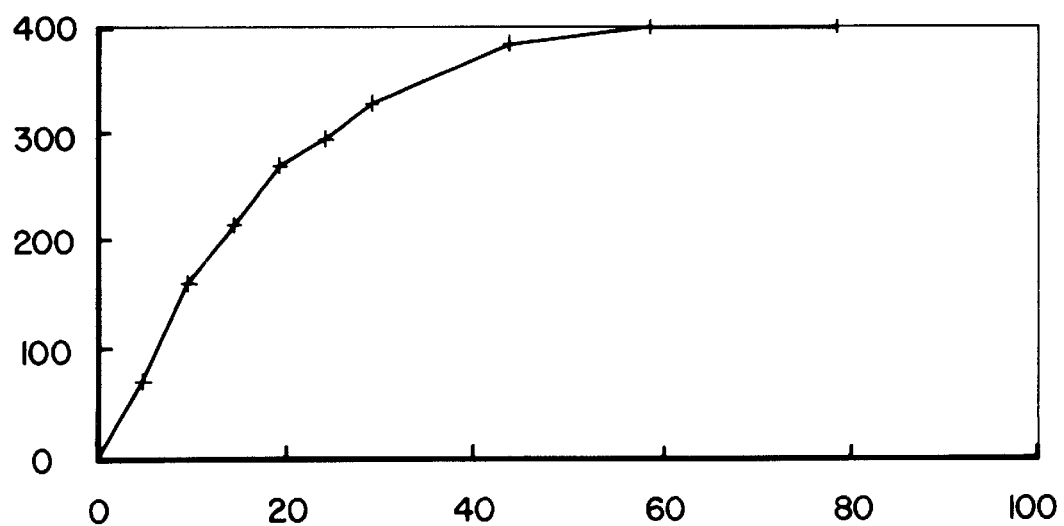
FIG. 7 is a plot of effusate glucose concentration (mgs/dL) vs effusion time (minutes), obtained using the second embodiment of the device. The gel of the device was composed of Carbopol 1 gram percent and glucose 400 mgs weight percent in water. The device was oriented with the membrane facing upwardly and a volume of water (50 or 100 $\mu$l) was place on the membrane. Glucose was allowed to effuse from gel across the membrane and into the drop of water where initial concentration of the glucose was zero. The concentration of glucose present in the known volume of water was measured at 10 minute intervals with an Elite Glucometer and plotted as a function of time.
Figure 8:
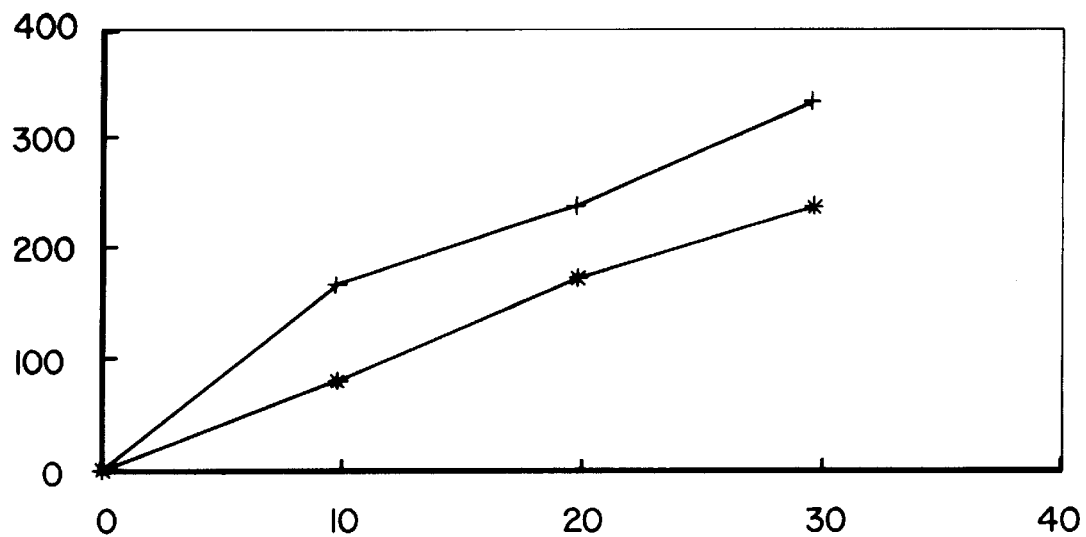
FIG. 8 is a representative plot of effusate glucose concentration (mgs/dL) vs effusion time (minutes), obtained using the second embodiment device after being placed in contact with a person's skin. The gel of the device was composed of Carbopol 1 gram percent and glucose 400 mgs percent. The top curve of the plot shows effusion of glucose from gel in a calibration experiment prior (pre) to application to skin. The bottom curve shows results obtained after (post) application of device to a person's wrist for 30 minutes.
Figure 9:
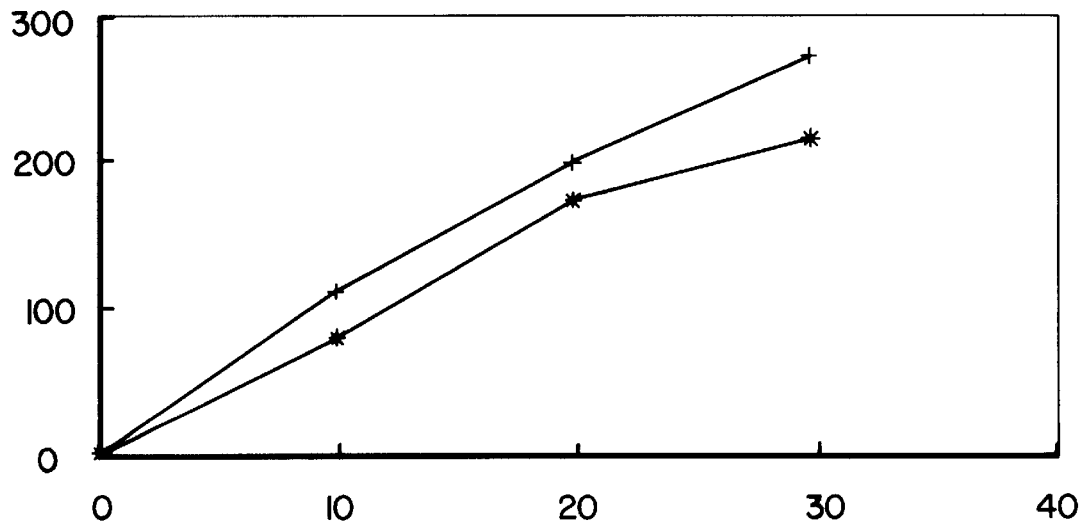
FIG. 9 is similar to FIG. 8 but in this case urea 5 gms percent was also included in the gel composition used to obtain the results.

Results obtained using device 22 are shown in FIGS. 7, 8 and 9. In one set of experiments (FIG. 7), a gel substrate (loaded with glucose, 400 mgs percent) was placed in the reservoir well and calibrated by measuring the concentration of glucose which had effused across the semipermeable membrane into a 100 $\mu$l drop of water placed on top of the semipermeable membrane (the device being in a position inverted to that shown in FIG. 6). FIG. 7 shows the concentration of glucose measured in the water droplet as a function of time. Conversion of concentration data to logarithmic form shows that the glucose effuses from the reservoir well into the water drop according to first-order kinetics for mass transfer, that is, that the transfer of glucose into the external volume of water is consistent with a diffusion-limited process.

In another set of experiments, the device was placed on the wrist of human subjects with the semipermeable membrane against the skin to permit glucose to diffuse from the reservoir well across the semipermeable membrane into the skin for thirty minutes. Thereafter, the calibration procedure was repeated to determine the remaining concentration of glucose. FIG. 8 shows the calibration procedure pre- (upper plot) and post-application (lower plot) of the device to skin of human subjects. The slower rate of effusion of glucose (post vs pre) from the reservoir chamber into a 100 $\mu$l water drop indicates that post glucose concentration is less than that of the pre condition. The difference in glucose concentration reflects the amount of glucose which diffused from the gel into the skin.

Similar experiments were carried out with a similar gel containing 5% urea, the results being shown in FIG. 9.

In another series of experiments, effusion of water from the skin was measured. Water taken up from the skin using an occlusive patch device similar to that shown in FIG. 1 was determined. In these experiments, however, no glucose was added to the paper prior to positioning the device on a person's skin. In a first set of experiments, the device was left in place for 30 minutes and then the paper was weighed. The person's blood glucose level was also determined directly using an Elite glucometer as described above. Representative data are plotted in FIG. 10. As can be seen, there is an increase in water absorbed by the paper from the skin with increasing blood glucose concentration.

Figure 11:
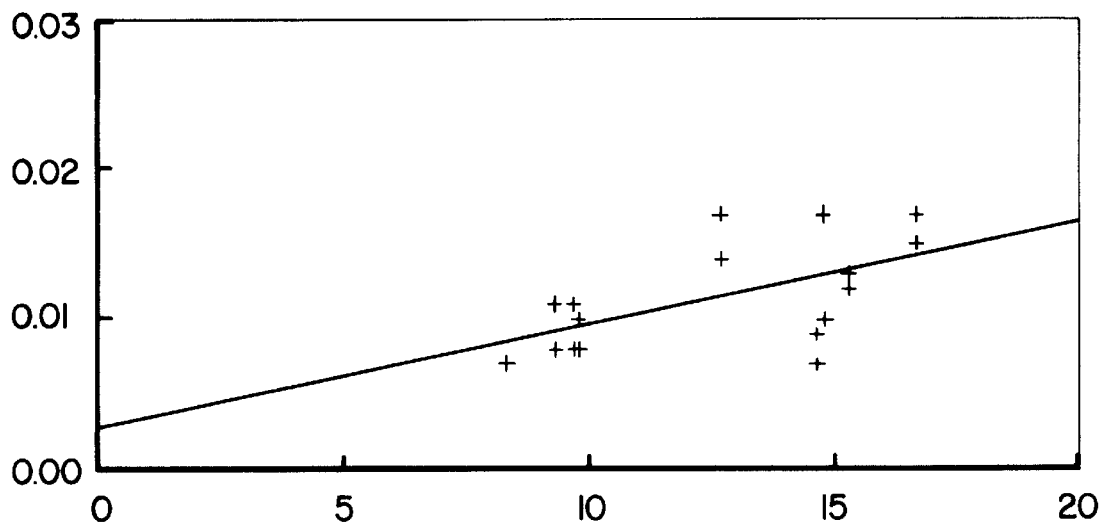
FIG. 11 is a plot of the concentration of glucose present in a paper substrate (first embodiment device) (absorbance at 505 nm) determined using the Trinder Glucose Reagent Kit, #315-100, (Sigma, St. Louis, Mo.) as a function of weight (mgs) of water absorbed and retained by the paper substrate from a person's skin over 30 minutes.

These experiments were extended by measuring the amount of glucose taken up by the paper substrate of the device as determined using a Trinder enzymatic assay. The amount of glucose (absorbance at 505 nm) plotted as a function of the amount of water taken up from the skin water (mgs) is shown in FIG. 11.

Figure 12:
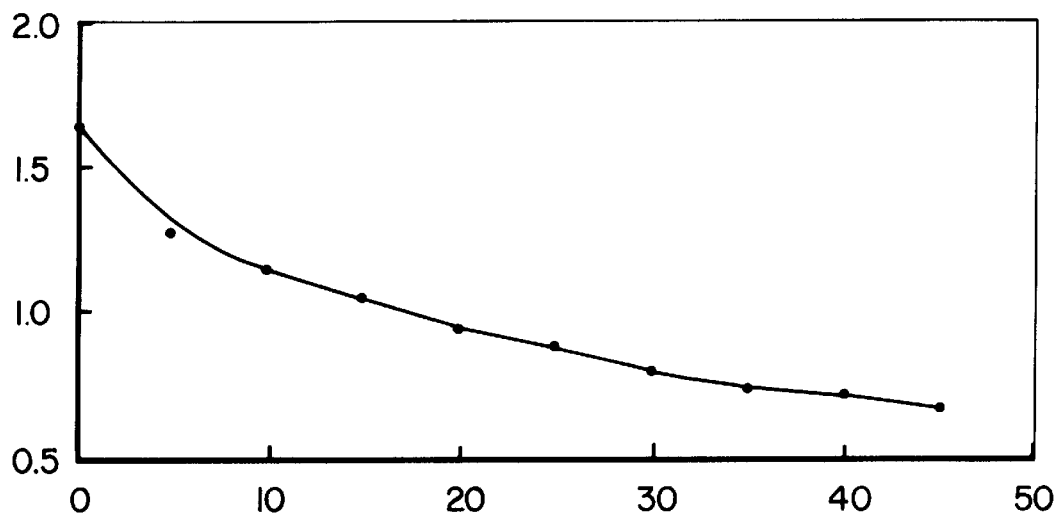
FIG. 12 is a plot of electrical resistance (MΩ) against time (minutes) as measured through an EKG type electrode used as an occlusive bandage for a paper substrate.
Figure 13:
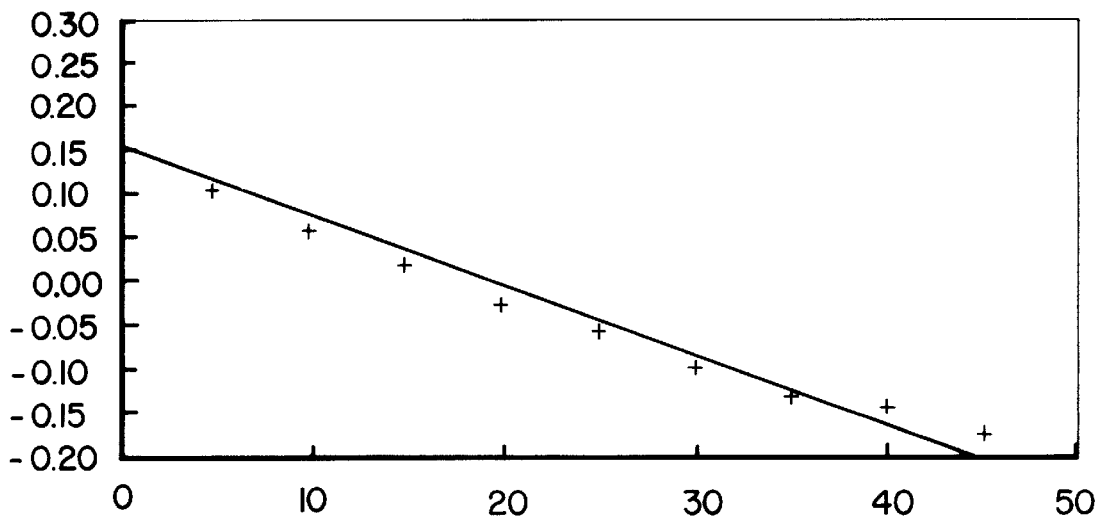
FIG. 13 show the data of FIG. 13 replotted as log resistance as a function of time (minutes)

A similar experiment was carried out in which occluded paper strips were analyzed for water absorbed and retained in situ using EKG type metal electrodes for occlusion, FIG. 1a. DC ohmmeter type instruments showed that retention of water under a metal electrode occlusion decreased DC resistance. See FIGS. 12 and 13. In FIG. 12, electrical resistance (M$\Omega$) is plotted as a function of time. In FIG. 13, log R is plotted as function of time, showing that the decrease in resistance is, at least approximately, a first order process. Blood glucose levels were also determined directly, as before, over time. The time taken for resistance to decrease a standardized amount (150×10$^3\Omega$) was plotted against the directly measured glucose level. See FIG. 14. As can be seen, the time for the resistance to decrease the standardized amount decreased with the directly measured blood glucose level.

Figure 15:
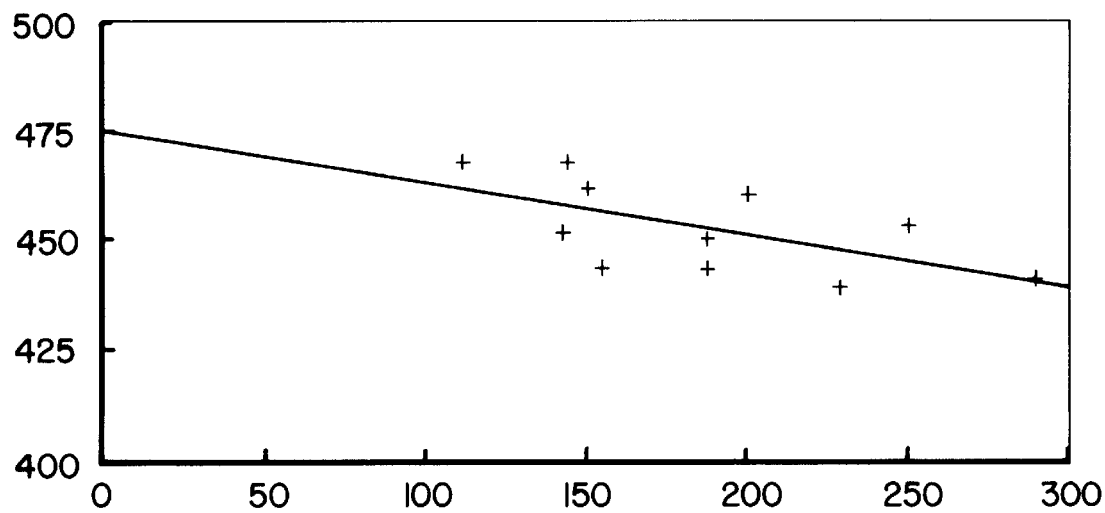
FIG. 15 is a representative plot showing glucose concentration (mgs/dL) retained in 0.4 ml of an aqueous solution contained in the well of a variant of the FIG. 6 device (see text) after exposure to a person's skin for 30 minutes as a function of the person's blood glucose level (Mgs/L) measured directly using an Elite Glucometer. Initial glucose concentration was 475 mgs/dL.

A modification of the FIG. 6 device was used to obtain the results shown in FIG. 15. In the modified device, upper plate 30 and collar 32b were replaced with an adhesive film. Lower membrane 26 and intermediate collar 32a were omitted, collar 32c remaining for adherence of the device to the skin. Well 24 was filled with a 0.4 ml of solution having a glucose concentration of about 475 mgs/dl and about 5 gms percent of propylene glycol. Propylene glycol is a wetting agent used to enhance diffusive contact of the aqueous solution of glucose with the skin. The device, oriented in a position inverted to that illustrated, was fixed to the skin by lifting the filled horizontal device to bring it into contact with the forearm of a subject held horizontally above the device. The arm with the device affixed thereto can be moved freely, without particular restraint, although care must be taken to avoid disturbing the device and to preclude detachment from the arm. After about thirty minutes, the arm was oriented with the device oriented upwardly with the outer film on top. The film was punctured and the electrode tip of an Elite Glucometer was inserted directly into the solution in the well of the device to measure the glucose concentration.

Blood glucose levels were determined as above and glucose level of the solution (mgs/dL) was plotted as a function of the blood glucose level. See FIG. 15. As can be seen, the glucose remaining in the device after 30 minutes decreases with increasing blood glucose level.

Another embodiment of the invention involves measurement of impedance at the skin surface. Experiments were carried out with measurements being taken with a dermal phase meter (DPM) available from Nova™ Technology Corporation of Gloucester, Mass. Measurements were taken at two skin sites, the forearm and the middle finger. The scale of the meter is from 90 to 999. Blood glucose measurements were also measured directly (Mgs/dL) using an Elite Glucometer, as described above. Measurements were taken at various times to track changes in skin hydration from that present while fasting overnight, attending ingestion of a typical meal for breakfast or lunch and following a peak of blood glucose and decline to about 100 Mgs/dL.

In these experiment, a probe sensor was placed against the skin surface and held lightly until the instrument indicated completion of data acquisition. Time interval (latch time) for data acquisition was selected at zero seconds (instantaneous). Other suitable time periods can be anywhere 0 and 30 seconds, or between 0.5 and about 10 seconds, or between about 1 and 5 seconds or about 5 seconds. The results obtained using the dermal phase meter are plotted as function of blood glucose concentration in FIGS. 16 and 17, respectively. Each plotted point represents the average of 10 measurements using the dermal phase meter.

Figure 10:
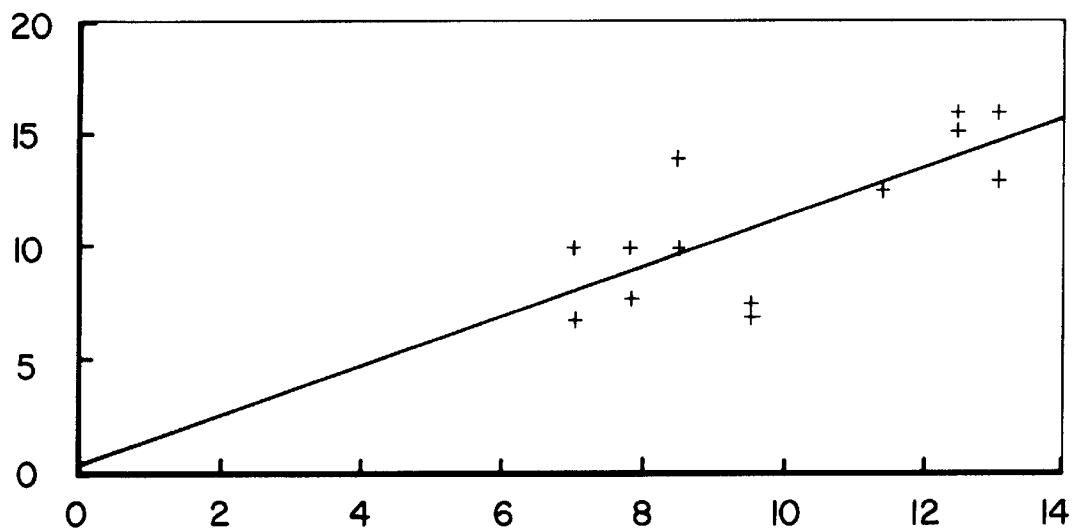
FIG. 10 is a plot of weight (mgs) of water absorbed and retained by a paper (first embodiment device) from a person's skin over 30 minutes as a function of the person's blood glucose level (Mmol/L) measured directly using an Elite Glucometer.
Figure 14:
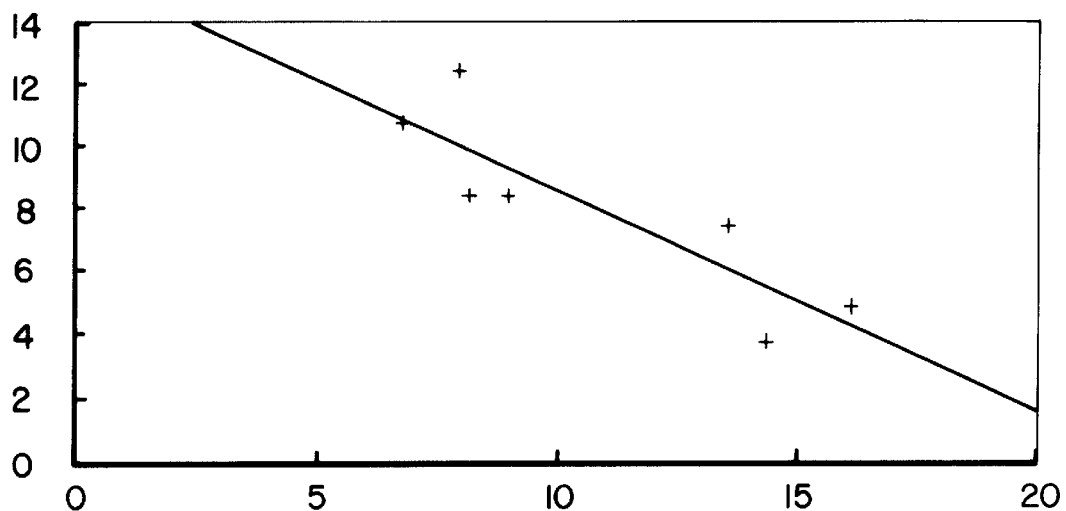
FIG. 14 is a plot of the time (minutes) taker for DC resistance to decrease a standardized amount ($150 \times 10^3 \Omega$) using the EKG type electrode as an occlusive backing for a paper substrate held against the skin of a person, plotted against the blood glucose level of the person, measured directly.
Figure 16:
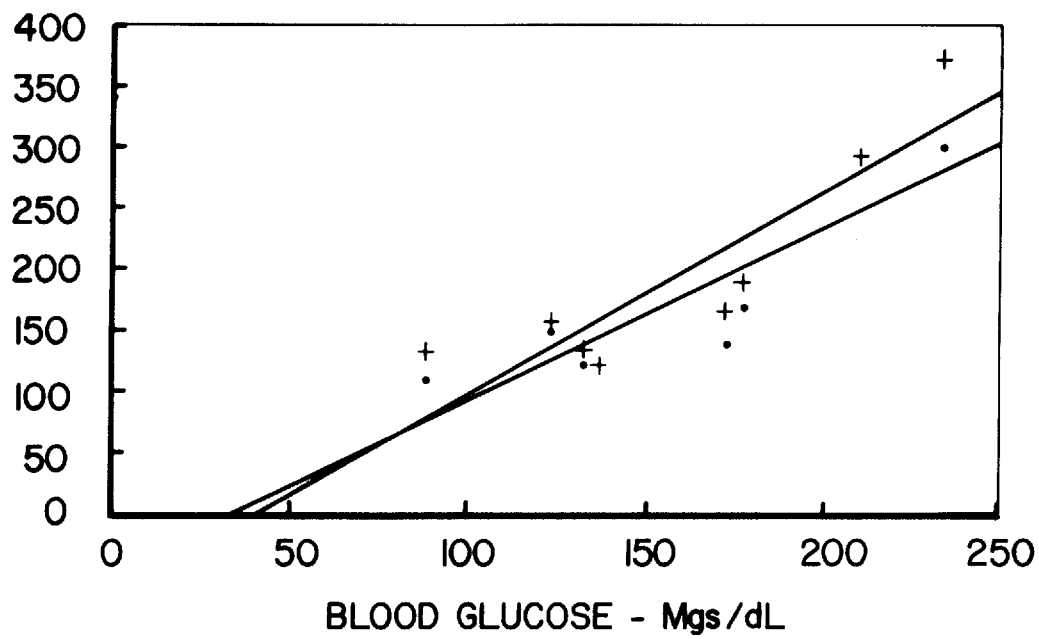
FIG. 16 is a plot showing the reading (average of ten readings) of a dermal phase meter as a function of directly determined blood glucose concentration. Measurements were taken on a site on the left forearm (•) and right forearm (+)
Figure 17:
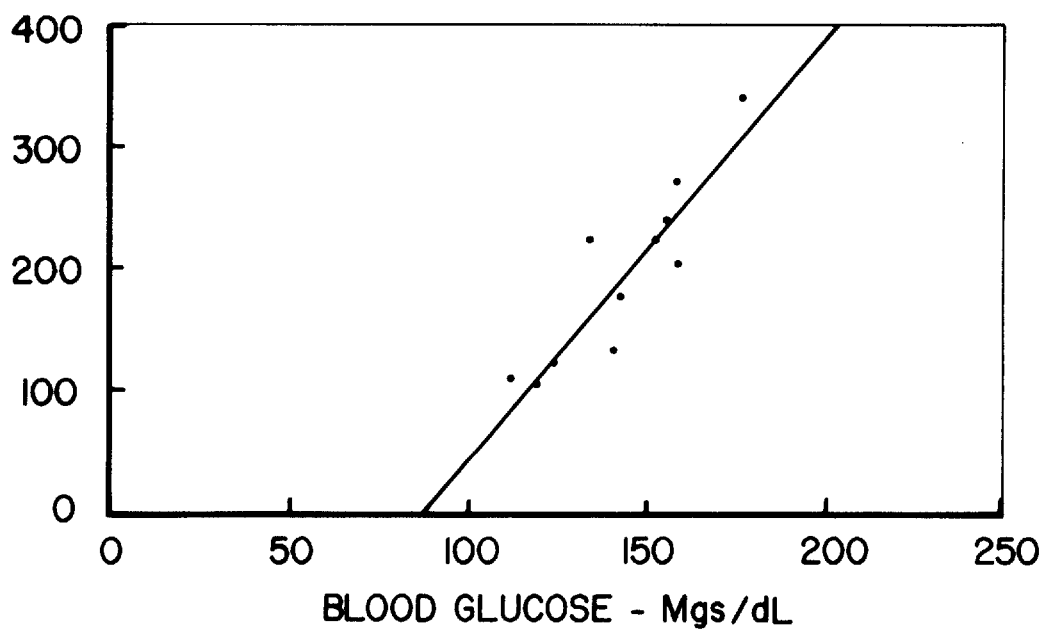
FIG. 17 is similar to FIG. 16, but the hydration readings were taken at a finger.

The data of FIGS. 10, 12 and 14 show that water absorbed by a paper substrate (for a fixed period of time) increases with increasing blood glucose concentration. The data of FIG. 11 show that the amount of glucose which migrates to a paper substrate (over a fixed time period) increases with increasing blood glucose concentration. It is thus clear that both water and glucose are capable of migrating through the corneum stratum of the skin. The data of FIG. 15 show that migration of glucose from water (of a device containing 0.4 ml of a 475 mgs/dl glucose in water solution) into the skin increases with increasing blood glucose. FIGS. 16 and 17 indicate that the degree of hydration of the skin increases with increasing blood glucose concentration.

A possible explanation for the foregoing observations is now given, although the inventor does not wish to be limited by any theory. The approach used to obtain the results shown herein, and in particular in FIGS. 15 to 17, can be used to non-invasively determine the blood glucose level of a subject and this benefit of the invention is not diminished by the presence or absence of the following explanation.

It is assumed that the pathway by which water travels into the skin is by means of interstitial spaces or channels. From the results of FIG. 10 it is inferred that the water contained in such interstitial spaces increases with increasing blood glucose concentration. As the glucose concentration of such interstitial fluid is reflective of blood glucose level, the glucose concentration in the interstitial fluid also increases with increasing blood glucose concentration. As an explanation for the downward slope of the data plotted in FIG. 15, a two-step process is proposed. Firstly, water from the device "hydrates" the skin. Water diffuses more rapidly than glucose from the device into the interstitial spaces to which it has access through the stratum corneum. There is a limit to the amount of water which can be contained in such spaces. In a second, slower step, but one which is promoted by increased hydration of the skin, glucose diffuses from the device into the interstitial channels. It would be expected that the rate of the second step would be in some proportion to the difference between the concentrations of glucose in the device and the interstitial spaces. In any event, since the degree of skin hydration increases with the blood glucose of the subject, "full" hydration of the skin through the first step of the process occurs more rapidly with increasing blood glucose concentration. This in turn means that the second step occurs more readily when the blood glucose of the subject is higher. It is thus observed that the amount of glucose which diffuses from the device into the skin increases with increasing glucose concentration. It is likely that the two steps of the process occur simultaneously to some extent (although at different rates), but the results of FIG. 15 indicate that the first step of the process predominates and hence the degree of glucose depletion from the device depends more on the initial degree of hydration of the skin than on the concentration of glucose in the interstitial spaces. The data plotted in FIGS. 16 and 17 indicate that the degree of skin hydration, measured over a relatively short period of time, increases with blood glucose concentration.

Figure 5:
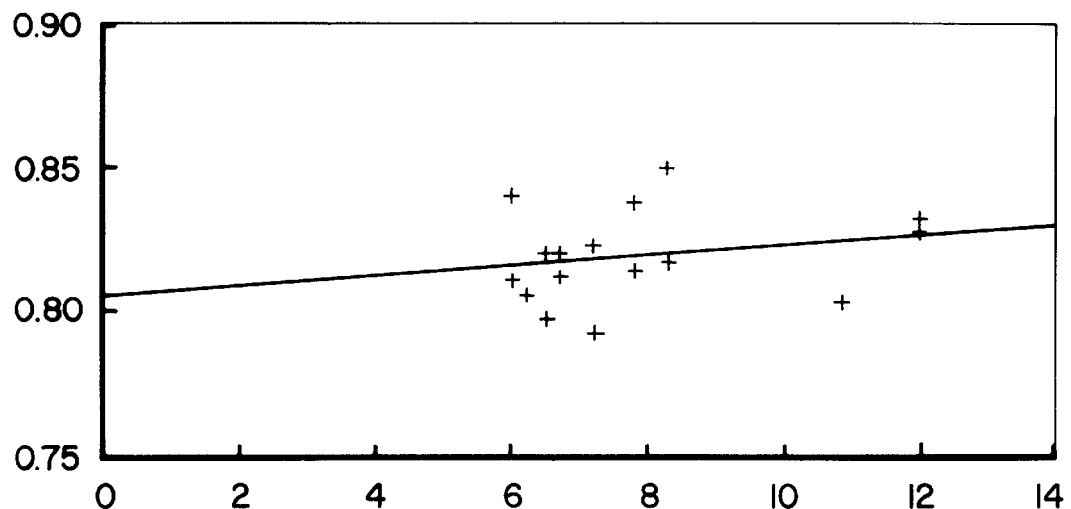
FIG. 5 is a plot of spectral absorbance (635 nm) of eluate of paper strips vs directly determined blood glucose level of human subjects (mmol/L). The conditions under which the experiments were conducted were similar to those described for FIGS. 3 and 4, but in this case, urea, 10 grams percent had also been applied to each paper strip.

Returning to the data plotted in FIGS. 3, 4 and 5, in which the substrate bearing glucose was paper, the substrate bears insufficient water for the hydration process to occur appreciably, the second step of the process predominates and hence the degree of glucose depletion from the paper substrate is inversely related to the concentration of glucose in the interstitial spaces and hence also to blood glucose concentration.

A substrate of the present invention, for use in connection with an aspect of this invention in which glucose is loaded to the substrate prior to use has the property that a suitable amount of glucose can be loaded to the substrate and retained by the substrate, subject to proper storage, until the substrate is brought into contact with skin A substrate for use in connection with an aspect of this invention in which glucose transfers to an unloaded substrate has the property that transfer, i.e., diffusion of the glucose into the substrate occurs readily.

The test subjects of the experiments described above were non-diabetic and free of any apparent endocrinological abnormality that would compromise the observed results. Studies were performed in the morning on fasting subjects. After baseline measurements on fasting, food was ingested to raise blood glucose levels. Studies continued until blood glucose levels declined to baseline levels.

In accordance with the theory proffered above for the results shown in FIG. 15, it is contemplated that a migratory substance other than glucose could be monitored in order to determine the blood glucose level of a subject. In one contemplated approach, an aqueous solution of a substance which, like water, migrates readily into interstitial spaces could be used. In a second alternative contemplated approach, an aqueous solution of a substance which, like glucose, migrates slowly into the interstitial spaces could be used. In either case, a substance that provides advantageous light-absorbance characteristics for convenient monitoring could be chosen. Further, since it might well be possible to use a substance which is not present in the interstitial spaces of skin (or occurs at a constant concentration therein) the rate of the second step of the process would be uncomplicated by the presence of the substance in the interstitial space, as could potentially cause problems with glucose. The use of such a substance would thus provide the added advantage that the diffusion thereof would be independent of glucose concentration and has the potential of providing even more reliable results than those obtainable through the monitoring of glucose.

The invention now having been described, including the best mode currently known to the inventor, the claims which define the scope of the protection sought for the invention follow.

What is claimed is:

1. A method for non-invasively monitoring glucose in a body fluid of subject, the method comprising:

continuously measuring impedance of the skin at a site of the outer skin of the subject; and quantitatively determining the amount of glucose in the body fluid based upon the measurement.

2. The method of claim 1 wherein the impedance is measured for a period of time between about just more 0 seconds and about 30 seconds.

3. The method of claim 2 wherein the time period is between about 0.5 seconds and about 10 seconds.

4. The method of claim 3 wherein the time period is between about 1 second and about 5 seconds.

5. The method of claim 3 wherein the time period is about 5 seconds.

6. The method of claim 1 wherein the impedance is determined at a site on the forearm or finger tip of the subject.

7. The method of claim 1 wherein the body fluid is blood.

8. The method of claim 1 wherein a plurality of said impedance measurements is taken and the determination is based on an average of said measurements.

* * * * *